United States Patent
Lehtonen-Krause

(10) Patent No.: US 7,365,538 B2
(45) Date of Patent: Apr. 29, 2008

(54) METHOD AND APPARATUS FOR MR IMAGE ACQUISITION WHEREIN OPERATING PARAMETER SETS ARE DISPLAYED WITH AN IMAGE ELEMENT INDICATIVE OF AN ACQUISITION RESULT

(75) Inventor: Sari Lehtonen-Krause, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/220,805

(22) Filed: Sep. 7, 2005

(65) Prior Publication Data

US 2006/0058635 A1    Mar. 16, 2006

(30) Foreign Application Priority Data

Sep. 7, 2004    (DE) .................. 10 2004 043 262

(51) Int. Cl.
 *G01V 3/00*    (2006.01)
(52) U.S. Cl. ..................................... 324/307
(58) Field of Classification Search ........ 324/300–322; 600/410–435
 See application file for complete search history.

(56) References Cited

U.S. PATENT DOCUMENTS

| | | | | |
|---|---|---|---|---|
| 5,759,152 A * | 6/1998 | Felmlee et al. | ............. | 600/410 |
| 6,249,595 B1 * | 6/2001 | Foxall et al. | ............... | 382/128 |
| 6,424,996 B1 * | 7/2002 | Killcommons et al. | ..... | 709/206 |
| 6,603,494 B1 | 8/2003 | Banks et al. | | |
| 6,721,590 B2 * | 4/2004 | Ohishi et al. | ............... | 600/431 |
| 7,022,073 B2 * | 4/2006 | Fan et al. | .................... | 600/437 |
| 7,090,640 B2 * | 8/2006 | Barth et al. | .................. | 600/443 |
| 7,123,766 B2 * | 10/2006 | Mao et al. | ................... | 382/154 |
| 7,148,688 B2 * | 12/2006 | Kojima | ........................ | 324/318 |
| 7,149,564 B2 * | 12/2006 | Vining et al. | ................ | 600/425 |
| 2003/0228042 A1 | 12/2003 | Sinha | | |
| 2004/0061630 A1 | 4/2004 | Rose | | |
| 2004/0081341 A1 | 4/2004 | Cherek et al. | | |
| 2004/0082846 A1* | 4/2004 | Johnson et al. | ............. | 600/410 |

FOREIGN PATENT DOCUMENTS

DE    199 53 308    6/2000

OTHER PUBLICATIONS

Patent Abstracts of Japan Publication No. 2000300538, for Japanese Application No. 11116258.

* cited by examiner

*Primary Examiner*—Brij Shrivastav
*Assistant Examiner*—Dixomara Vargas
(74) *Attorney, Agent, or Firm*—Schiff Hardin LLP

(57) ABSTRACT

In a method and MR apparatus for acquisition of images of an examination region of a human or animal body by means of measurement parameter sets controlling the image acquisition, selection of an examination region to be acquired is made by a user according to anatomical viewpoints by means of a whole-body representation of an image element of the body (stored in a storage region for image data) on a monitor. A list of measurement parameter sets for the selected region is displayed on the monitor, with the measurement parameter sets in the list each being shown with at least one region-specific image element (stored in a storage region) of an acquisition result that can be obtained with this measurement parameter set. A measurement parameter set for image acquisition is then selected.

13 Claims, 2 Drawing Sheets

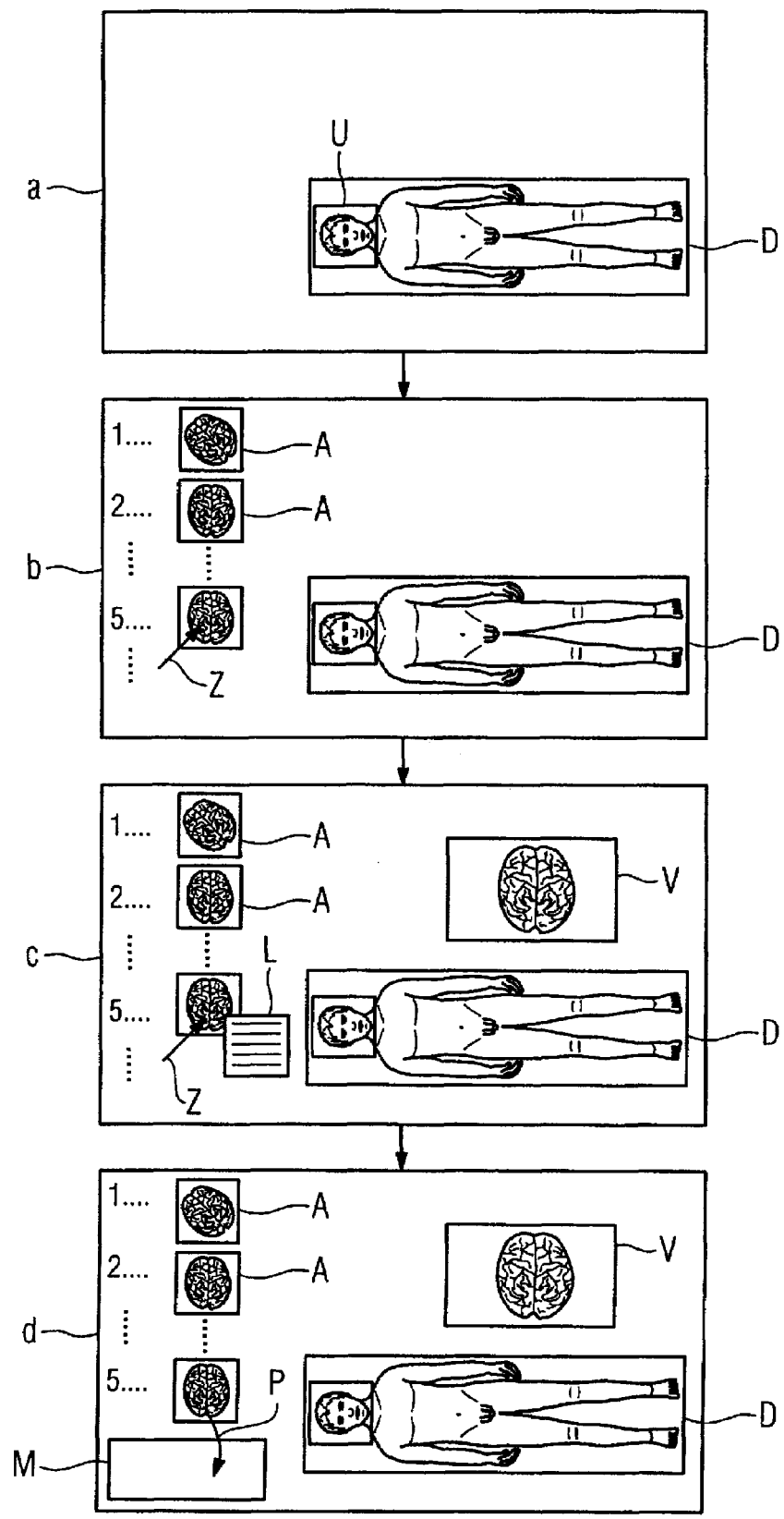

METHOD AND APPARATUS FOR MR IMAGE ACQUISITION WHEREIN OPERATING PARAMETER SETS ARE DISPLAYED WITH AN IMAGE ELEMENT INDICATIVE OF AN ACQUISITION RESULT

BACKGROUND OF THE INVENTION

1. Field of the Invention

The present invention concerns a method and MR apparatus for the acquisition of images of an examination region of a human or animal body in a magnetic resonance system by means of measurement parameter sets controlling the image acquisition.

2. Description of the Prior Art

The measurement parameter sets available in a magnetic resonance system, which are either predetermined at the manufacturer or are applied by a customer, are listed in a program available to an operator. From this list the user can select measurement parameter sets that are to be used for acquisition of images in the magnetic resonance system. In order to find a specific measurement protocol, the user must search through an index tree in which different examination regions are listed by their names. Under the circumstances, the user thus must read almost all entries of this index tree in order to find and select the desired examination region so that the parameter sets provided for this examination region are shown. An overview of the entirety of the available measurement parameter sets is difficult. Operators who do not work with the system every day require a relatively long time in order to search out a specific parameter set using the list of the names of the examination regions.

SUMMARY OF THE INVENTION

An object of the present invention is to provide a method and MR apparatus for the acquisition of images in a magnetic resonance system that avoids the disadvantages of known methods and systems.

This object is achieved in accordance with the invention by a method for the acquisition of images of an examination region of a human or animal body in a magnetic resonance system by means of measurement parameter sets that control the image acquisition, wherein selection of an examination region to be acquired according to anatomical viewpoints is made by a user using a whole-body display of an image element of the body (stored in a storage region for image data) on a monitor, a list of measurement parameter sets for the selected region is displayed on the monitor, with the measurement parameter sets in the list each being shown with at least one image element (stored in a storage region and being region-specific) of an acquisition result that can be acquired with this measurement parameter set, and a measurement parameter set for image acquisition is selected using the displayed list.

In accordance with the invention, the user initially sees a whole-body representation, for example an icon or a representative whole-body exposure, in which the user can select the desired examination region, for example via a selection tool that is operated by a keyboard, a mouse or a joystick or the like. The examination region for which the associated measurement parameter sets are to be used for image acquisition is sought, or the examination region for which a specific measurement parameter set is sought in order to ultimately implement an acquisition, is selected by the user according to anatomical viewpoints. This means that the user can become oriented on the intuitively-recognizable image representation of the body. In this manner the region of interest can be found quickly without knowledge of a specific sequential structure (tree) having to be employed by the user.

The display of the list of measurement parameter sets for the selected region is subsequently generated on the monitor, with measurement parameter sets predetermined by the manufacturer and customer-specific sets both being able to be shown. The selection of a measurement parameter set for image acquisition ultimately ensues using this list. The operator of the magnetic resonance system has the advantage of selecting the examination region directly using an image element without searching in a list. This allows a significantly faster and simpler overview of the existing protocols or sequences.

The measurement parameter sets in the list preferably are each shown with at least one region-specific image element (stored in the storage region) indicative of an acquisition result that can be obtained with this measurement parameter set. Using the image element indicative of an acquisition result, it is apparent to the user which image quality is to be expected given an acquisition with this parameter set, or which diagnostic information can be acquired for which tissue types with this parameter set. Data that otherwise could only be laboriously obtained from a patient databank (in which the measured image data are stored only until they are deleted with the remaining data for the corresponding patient) are therewith accessible to the user at this point.

A sought measurement protocol can easily be found in an embodiment wherein an overview of the acquisition results of the respective examination region is provided. Using the overview of the image elements, in addition the protocol the user originally considered, the user is additionally prompted to make use of a possibly better-suited protocol that is indicated to the user by the image element of the protocol result. The intuitive ascertainability of image elements (possibly augmented by a generalized text rep representation) is thus used in a targeted manner in order to ensure that the image acquisition ensues with optimal parameter sets.

Furthermore, an image element indicative of an acquisition result, the image element being associated with a measurement parameter set, can be selected in the list by the user. For example, this can be clicked-on by means of a mouse pointer or can be contained in the region of the selection tool (for example a box).

In a further embodiment of the invention, the image element is shown enlarged upon a selection thereof being made. This can occur, for example, when a mouse pointer is moved over the image element. The enlarged representation allows a still-better assessment of the image quality or of the diagnosis to be assessed using such an acquisition.

In addition, given a selection of the image element the parameter of the associated measurement parameter set can be indicated. For example, for this purpose a parameter card or list, to which the user has a read-access right, can be opened, for example by a double-click on the image element of a specific head acquisition.

According to the invention, a measurement parameter set for image acquisition can be directly selected and/or (if applicable) selected by an associated image element, such as clicking or sliding. Via this selection, the special measurement parameter set arrives in a measurement queue via which the workflow of the image acquisitions is determined. This can ensue, for example, by clicking on the parameter set name or the parameter set image, or the measurement parameter set can be directly shifted into the measurement queue by "drag and drop" using the name or the image.

In addition, at least one image element in accordance with the invention can be a component of a library. The storage of image elements in a structured image library enables a simple and clear administration of such available images. It is thus clear at any time where an image element is stored, so that it can be quickly replaced by a new element if necessary. In addition, for the operator of the system it is simple, given use of a library, to hold the image elements in a current state. Using this library, if necessary the image elements can be accessed by a number of relevant programs in the magnetic resonance system in connection with the image acquisition.

Given the storage and/or optimization and/or editing of user-specific measurement parameter sets and/or measurement parameter sets obtained from external data sources, associated image elements are recorded (entered) in the library. When the user changes individual parameters of the parameter sets, the user can thus directly record in the library an image element of an acquisition result associated with the changed parameter set. The same applies when a new measurement parameter set is to be added. Thus, for example, protocols from the Internet or from other customers that work with magnetic resonance systems (if applicable, already with associated acquisition results) can be adopted, whereby the image elements are directly incorporated into the image library.

In a further embodiment of the invention, measurement parameter sets that are already provided with at least one image element are optimized and/or edited by a selection of the image element. Thus, for example, processing of the individual parameter can be enabled via a right click on the respective image element. In addition to this, an editing can also be enabled by selection of the image element, thereby allowing the user to note specific remarks or instructions regarding the respective parameter set or acquisition result shown in the image element. These remarks or instructions are then respectively visible only upon a special selection of the image element (thus, for example, only given selection by a right click).

A number of items of information are available to the user dependent on the users desire, without the representation in the list of the parameter sets being overloaded. Without a selection of the image element, the user receives only the acquisition result in the form of the image element or the names of the protocol; auxiliary information, however, is easily accessible at any time.

The measurement parameter sets can likewise be stored in the library for the image elements, or in at least one further library. Storage is undertaken dependent on the total amount of data that exists in the combination of all measurement parameter sets, or dependent on how the linking between parameter sets and image elements should be executed. Among other things, given very extensive data quantities, sub-libraries can be provided, for example for individual examination regions.

The library for the image elements preferably is opened via a menu or a link of programs encompassing all existing measurement parameter sets After clicking on a corresponding menu point or symbol or a link, the user in this case receives the representation of the body on the monitor. If the corresponding link or menu point is not addressed, an image acquisition can be implemented without the use of image elements. It is thus left up to the user whether to use the library.

The invention also encompasses a magnetic resonance system that is suitable for implementation of the method described above. The magnetic resonance system has a magnetic resonance scanner and a control unit as well as a monitor. The control unit has (or has access to) a storage region for image data in which an image element is stored that can be represented as a whole-body representation on the monitor for selection of an examination region to be acquired.

For display of a list of measurement parameter sets existing for the selected region, the magnetic resonance system allows selection of a measurement parameter set for image acquisition, with at least one region-specific image element (stored in the storage region) of an acquisition result that can be obtained with this measurement parameter set on the monitor.

DESCRIPTION OF THE DRAWINGS

FIG. 2 schematically illustrates the implementation of an embodiment of the inventive method.

DESCRIPTION OF THE PREFERRED EMBODIMENTS

Figure 1:
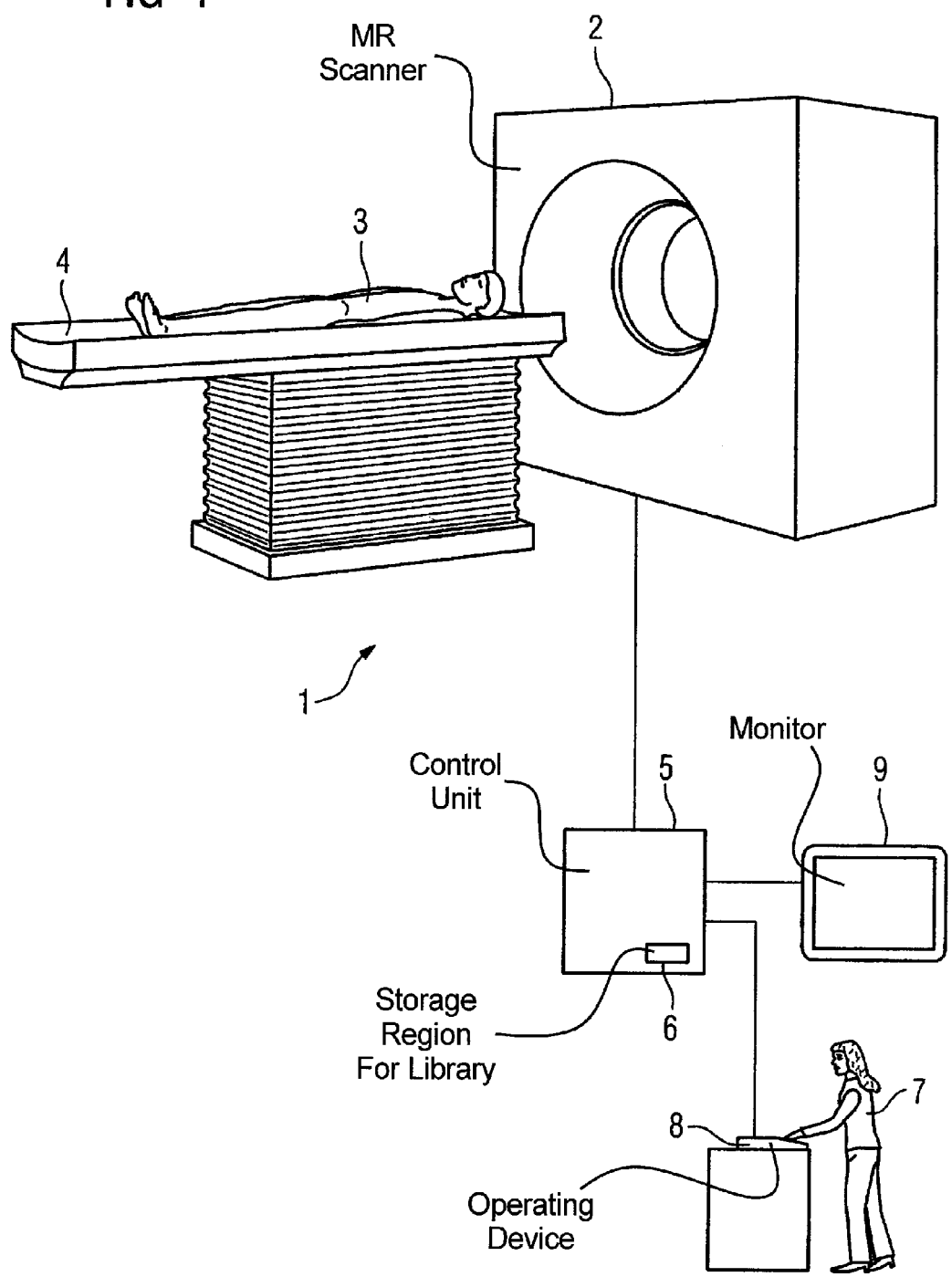
FIG. 1 schematically illustrates the basic components of an inventive magnetic resonance system.

FIG. 1 shows an inventive magnetic resonance system 1. The magnetic resonance system 1 has a magnetic resonance scanner 2 into which a patient 3 is inserted for examination on a patient table 4. The image acquisition operation of the magnetic resonance system 1 is controlled by a control unit 5 that has a microcomputer with a storage region for, among other things, an image library 6.

In the control device 5, the acquired data are processed and the parameter sets for images to be acquired are translated into control instructions for the magnetic resonance scanner 2. The magnetic resonance system 1 is operated by an operator 7 by means of an operating device 8, for example a keyboard or a computer mouse, using the representation on a monitor 9. With the control unit 5, the opening of the image library 6 is enabled to the operator 7 on the monitor 9 via a menu point. The operator thereupon obtains a whole-body representation of a body on the monitor 9. There the operator can select a desired examination region by means of the operating device 8, for which examination region all existing measurement parameter sets are shown that are provided by the manufacturer and/or the user.

The representation ensues by means of image elements that the operator 7 can address via the operating device 8, such that the acquisition result shown in the image element (which acquisition result is obtained with the respective measurement parameter set) is shown enlarged. The parameters of the measurement parameters can additionally be displayed or altered by selection of an image element of an acquisition result. If a measurement parameter set is now selected for image acquisition via an image element of an acquisition result by the operator 7, it is included in a measurement series serving for implementation of the image acquisition. By movement of the patient table 4, the corresponding examination region of the patient 3 is brought into the center of the homogeneous magnetic field; the measurement parameters of the measurement parameter set are translated by the control unit 5 into the control signals for the magnetic resonance system 1. The image acquisition then is implemented.

By the use of the image library 6, it is easy to locate specific measurement parameter sets with the inventive magnetic resonance system 1 since an examination region is simply selected using the representation of the body according to purely anatomical viewpoints. A search through a long list is no longer necessary.

FIG. 2 schematically illustrates the implementation of an embodiment of the inventive method. The image library 6 that contains the image elements has already been opened in step a, and the user sees a whole-body representation D on a monitor. An examination region U is selected in this whole-body representation D by the user, for which a selection tool that is used can be moved with the operating device 8, such as a joystick or a computer mouse.

In step b a list of measurement parameter sets for this selected examination region U is thereupon shown with the name of the measurement parameter set and an acquisition result A that can be obtained with this measurement parameter set. Using the image representation of the acquisition result A, it is apparent for the user which image quality is to be expected given the use of the respective parameter set, or for which tissue type information particularly well-suited for the diagnosis can be acquired using the acquisition, which is additionally communicated to the user, if applicable, using text information.

As a result, in step c the image element of the acquisition result A is shown enlarged for the fifth parameter set, such that a better assessment of the image quality of the corresponding acquisition result A is possible in this enlarged representation V.

Given a new selection of the acquisition result A for the fifth measurement parameter set (which, for example, ensues by a right click using the mouse point Z), the parameters of the associated parameter set are displayed in a list L. An editing or optimization of the parameter sets can likewise be enabled via a selection of the corresponding image element of the acquisition result A. New parameter sets (for example parameter sets that can be obtained from the manufacturer via the Internet) are identically incorporated with associated image elements of an image library into the index of the measurement parameter sets.

If the user has decided to implement an image acquisition with the fifth parameter set, the user selects the image element of the acquisition result A for the fifth parameter set, by shifting it (as indicated by the arrow P in the step D) into a measurement queue M in which the parameter sets are listed for actual acquisitions to be implemented.

A significantly faster and simpler overview of the existing measurement protocols or measurement sequences is impossible with the inventive method. A region of interest U can be selected using an anatomical whole-body representation D without having to read through a list. The acquisition results A belonging to this examination region U are shown to the user in the list of the measurement parameter sets so that, without additional effort, the user receives a perception of which exposures are to be expected given a selection of the corresponding parameter set. The image elements additionally enable processing of the parameter sets given a selection by means of different selection types. Given a change of the individual parameters of a set, the image element in the library can be replaced by a current one so that it is ensured that an acquisition is not perhaps conducted in the expectation that the originally stored measurement parameter set is still used. Overall more information is clearly available to the user than in a conventional listing of measurement protocols, while at the same time the clarity is maintained and additionally the locating of individual protocols is made easier.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for acquiring images of an examination region of a subject in a magnetic resonance system having a computer that controls operation of the magnetic resonance system, comprising the steps of:
   displaying an image element comprising a whole-body representation of the subject on a monitor connected to the computer;
   by electronic interaction of a user with the computer, selecting an examination region of the subject, from which magnetic resonance image data are to be acquired, by designating anatomical viewpoints in said whole-body representation;
   for the selected examination region, displaying a list of data acquisition parameter sets at said monitor and, with each of the displayed parameter sets, displaying an associated region-specific image element indicative of an acquisition result that can be obtained from the selected examination region using the associated parameter set; and
   via said computer, allowing the user to select one of the displayed parameter sets for operating the magnetic resonant system to acquire magnetic resonance data from the subject.

2. A method as claimed in claim 1 wherein said magnetic resonance system comprises a memory accessible by said computer, and comprising the steps of storing each of said image element comprising said whole-body representation, and the region-specific image elements respectively associated with said parameter sets, and retrieving, via said computer, said image element comprising said whole-body representation and said region-specific image elements from said memory for display on said monitor upon an entry into the computer by the user.

3. A method as claimed in claim 1 wherein the step of selecting one of said parameter sets for operating said magnetic resonance system by selecting, via interaction of the user with said computer, one of said region-specific image elements.

4. A method as claimed in claim 3 comprising the step of, upon selection of said one of said region-specific image elements by said user, displaying an enlargement at said monitor of the selected region-specific image element.

5. A method as claimed in claim 3 comprising, upon selection of said one of said region-specific image elements, displaying respective individual parameters of the parameter set associated with the selected region-specific image element.

6. A method as claimed in claim 1 wherein the step of selecting one of said parameter sets for operating said magnetic resonant system comprises selecting one of said parameter sets for operating said magnetic resonant system by user interaction with said computer selected from the group consisting of making a mouse-click and operating a displayed sliding control element.

7. A method as claimed in claim 1 wherein said magnetic resonant system comprises a memory accessible by said computer, and comprising storing said region-specific image elements as respectively library entries in a library in said memory.

8. A method as claimed in claim 7 comprising allowing entry into said computer of modified versions of said parameter sets, and new parameter sets, and upon entry of a modified parameter set, said computer automatically associating a new region-specific image element in said library with the respective modified or new parameter sets.

9. A method as claimed in claim 8 comprising automatically optimizing or editing one of said parameter sets upon selection of one of said region-specific image elements from said library.

10. A method as claimed in claim 7 comprising also storing said parameter sets in said library.

11. A method as claimed in claim 7 comprising storing said parameter sets in a further library accessible by said computer.

12. A method as claimed in claim 7 comprising opening said library for said region-specific image elements via a menu or a link, at said display, of a computer program comprising all of said parameter sets.

13. A magnetic resonance system comprising:
   a magnetic resonance scanner adapted to interact with a subject therein to obtain magnetic resonance data;
   a computer connected to said magnetic resonance scanner that controls operation thereof to obtain said magnetic resonance data using a parameter set;
   a monitor connected to said computer that displays an image element comprising a whole-body representation of the subject;
   a user interface connected to the computer allowing electronic interaction by a user with the computer to select an examination region of the subject, from which said magnetic resonance image data are to be obtained, by designating anatomical viewpoints in said whole-body representation;
   said computer, for the selected examination region, causing a list of data acquisition parameter sets to be displayed at said monitor and, with each of the displayed parameter sets, causing an associated region-specific image element to be displayed that is indicative of an acquisition result that can be obtained from the selected examination region using the associated parameter set; and
   said interface allowing the user to select one of the displayed parameter sets for operating the magnetic resonant system to obtain said magnetic resonance data from the subject.

* * * * *